United States Patent [19]

MacMichael et al.

[11] Patent Number: 5,914,262
[45] Date of Patent: Jun. 22, 1999

[54] PROCESS AND APPARATUS FOR CELL SORTING

[75] Inventors: Donald Bruce Atherton MacMichael, Hitchin; David Drake, Letchworth; Stephen Adrian Arlington, Southgate; Ian David Normansell, Worthing; John Kenneth Addicott, Worthing; Moira Sloan Divers, Worthing; John Spencer Stovold, Worthing, all of United Kingdom

[73] Assignee: SmithKline Beecham p.l.c., Brentford, United Kingdom

[21] Appl. No.: 08/556,920

[22] PCT Filed: May 17, 1994

[86] PCT No.: PCT/EP94/01641

§ 371 Date: Jun. 21, 1996

§ 102(e) Date: Jun. 21, 1996

[87] PCT Pub. No.: WO94/28119

PCT Pub. Date: Dec. 8, 1994

[30] Foreign Application Priority Data

May 21, 1993 [GB] United Kingdom .................. 9310557

[51] Int. Cl.⁶ ............................. C12N 1/00; B07C 5/02; G01N 21/00; A01N 63/00
[52] U.S. Cl. ........................... 435/243; 209/3.1; 209/511; 209/552; 209/576; 356/73; 424/93; 424/493; 435/177; 435/178
[58] Field of Search ............................. 209/3.1, 511, 552, 209/576; 356/73; 435/177, 178, 243; 424/93, 493

[56] References Cited

U.S. PATENT DOCUMENTS

| | | | |
|---|---|---|---|
| 4,175,662 | 11/1979 | Zold | 209/552 |
| 4,647,536 | 3/1987 | Mosbach et al. | 435/177 |
| 5,030,002 | 7/1991 | North, Jr. | 356/73 |
| 5,277,320 | 1/1994 | Corkill et al. | 209/511 |

*Primary Examiner*—James C. Housel
*Assistant Examiner*—Rodney P. Swartz
*Attorney, Agent, or Firm*—James M Kanagy; Charles M Kinzig

[57] ABSTRACT

A method of distinguishing between microorganisms having different attributes comprises the steps of: encapsulating one or more cells within a polymeric bead; incubating the cell(s) within the bead in a growth-supporting medium for a time period sufficient for multiplication of viable cells within the bead; then non-invasively physically examining the bead or the adjacent vicinity of the bead for physical characteristics associated with the differing attributes of cells within the bead. Various forms of apparatus for carrying out the process are descried.

15 Claims, 6 Drawing Sheets

PROCESS AND APPARATUS FOR CELL SORTING

SCOPE OF THE INVENTION

This invention relates to a novel method of microbial screening, and to a novel apparatus for carrying out the method.

BACKGROUND OF THE INVENTION

In the fields of microbiology, fermentation etc. it is frequently necessary to screen microbial cultures to distinguish between cells with different attributes or identify cells with similar attributes, for example viable and non-viable cells, or the level of productivity of a useful metabolite. One field in which such screening is particularly useful is in biotechnology, where microbial line development involving mutation of cells by mutagenic radiation or chemicals is carried out. After a microbial culture has been exposed to mutagenic influences it is necessary for the culture to be screened to detect mutations of interest. As the ratio of useful mutations to useless mutations is usually very low and the number of cells to be screened is usually very large it is desirable that fast and effective, ideally automated, processes are provided to carry out as much as possible of the screening.

Automated cell screening apparatus are known, but at present these can only screen relatively small numbers of cultures per year, and there is a need to improve on the rate of screening.

SUMMARY OF THE INVENTION

The inventors have developed a novel, improved microbial screening process and apparatus for carrying this process out.

According to a first aspect of this invention, a method of distinguishing between microorganisms having different attributes comprises the steps of:

encapsulating one or more cells within a polymeric bead;

incubating the cell(s) within the ad in a growth-supporting medium for a time sufficient for multiplication of viable cells within the bead;

then non-invasively physically examining the ad or the adjacent vicinity of the bead for physical characteristics associated with the differing attributes of the cells within the bead.

DESCRIPTION OF THE DRAWINGS

An apparatus and method of this invention will now be described by way of example only with reference to the following figures.

DETAILED DESCRIPTION OF THE INVENTION

The term "cell" used herein includes bacterial cells, animal or plant cells, fungal or bacterial spores (including conidia), microbial protoplasts and mycelial fragments. Example of suitable cells include spores of *Penicillium chrysogenum* and *Streptomyces clavuligerus*.

The method may be optionally followed, after further incubation, by the further step or steps of separating beads which contain cells possessing a selected attribute from beads which do not contain such cells, for example separating beads which contain multiplied viable cells from beads containing non-viable cells, or separating beads which contain one type of cell from beads which contain another type, or separating beads which contain cells which differ in their degree of viability and/or level of growth. This may then be followed by a yet further step of culturing and growing the viable cells on a larger scale, which may in turn be followed by a yet further step of examining and/or screening the grown viable cells for some useful characteristic. This may ultimately be followed by large scale fermentation.

The cells may be for example fungal or microbial spores. The method is particularly suited to screening for viable cells subsequent to exposure of the cells to a mutagenic influence, prior to subsequent screening for usefulness, e.g. secretion of a cell product such as an antibiotic.

Preferably a single cell is encapsulated within each bead.

Methods of encapsulation of single cells within polymeric beads are known. The polymeric bead is suitably an alginate polymer bead, in particular a calcium alginate polymer bead. One suitable method of encapsulation is to suspend the cells in a dilute (e.g. 1–5% suitably ca. 2–3%), preferably sterile solution of sodium alginate, and then to admix this suspension with a dilute (e.g. 0.05–1M, suitably ca. 0.1M), preferably sterile solution of calcium chloride. Admixing is suitably carried out by dripping the cell suspension into the stirred calcium chloride solution, e.g. via a needle tube assembly, so that calcium alginate polymer forms as a precipitated bead. By selection of a suitable dilution based upon the initial cell suspension concentration such that the volume of each droplet formed in the dripping process may contain on average no more than one viable cell, each bead produced in this way may contain on average no more than one viable cell. A suitable diameter for the beads is 3 mm±1 mm, e.g. around 3 mm diameter. A suitable cell dilution is consequently in the region 1 to $4 \times 10^4$ cells $L^{-1}$, e.g. around $2.5 \times 10^4$ cells $L^{-1}$.

The beads may be hardened by further immersion in calcium chloride solution, for example by suspension in saw in the solution in which they are formed, and/or by subsequent immersion in a more concentrated calcium chloride solution, e.g. 0.5–2.5M, suitably 1.0M. Beads may be prepared using stronger solutions of alginate where extensive growth may occur, or to restrict biomass to within the bead. The beads may subsequently be washed with water, suitably until the washings are substantially free of dissolved calcium. The beads may optionally be coated, e.g. by a further alginate deposit.

Such beads are porous, and incubation of cells within the bead in a growth-supporting medium may conveniently be carried out by suspending the beads in a medium appropriate to the cells in question, and at suitable incubation conditions of temperature, pressure, aeration etc., as will be apparent to those skilled in the art. To produce strong, robust beads it is desirable in the medium to avoid compounds or ions which sequester or exchange with calcium, for example citrate, potassium or sodium.

The medium is suitably a weak, defined medium, as such a medium has been found to encourage growth of the cells within the beads. A suitable growth-supporting medium is a 2% lactose based medium containing yeast extract as a nitrogen source and a basal nutrient solution, for example a medium derived from that described in Kuek, Appl. Microbial Biotechnol (1991), 35, 466–470 using lactose instead of starch as the carbon source. Another suitable medium is one containing L-asparagine, dextrin, $K_2HPO_4$, $MgSO_4$ and trace elements. Other suitable media will be apparent to those skilled in the art. The time period for multiplication will either be apparent to those skilled in the art from knowledge of the cells, or else may easily be determined experimentally, e.g. by the subsequent physical examination step described below.

At the end of this stage, among the beads there will normally be heads which are either empty of cells or which contain only non viable cells, and heads which contain one or more viable cells (and which may also contain non-viable cells). Beads which contain one or more viable cells are usually of principal interest, and viable cells will often manifest substantial cell growth and multiplication.

Beads which contain only non-viable cells will differ in their physical characteristics from beads which contain multiplied viable cells as a consequence of the larger proportion of biomass in the latter. Multiplied viable cells may also differ in their degree of viability or level of growth, and this may result in a differing proportion or distribution of biomass among beads which contain viable cells. These differences too will be manifest in differing physical characteristics. Such different physical characteristics may be inherently detectable upon examination, or it may be necessary or desirable to subject the beads to some enhancement process prior to examination, for example chemical staining etc, to enhance the physical characteristic which is the subject of the examination.

Differences in physical characteristics of the heads may result in differences in physical characteristics of the adjacent vicinity of the head, for example of a medium in which the bead is suspended.

The differences in physical characteristics may be differences in visual characteristics, detectable by the naked eye or under magnification, or to a video camera linked to suitably programmed image processing equipment. The differences may be differences in optical characteristics such as transmissivity, reflectivity, colour, polarisation etc. The differences may be differences in other physical characteristics such as electrical conductivity, capacitance, inductance, permeability to microwaves, ultrasound, or other radiation etc. Differences in physical characteristics of the vicinity of the bead may for example be differences in ionic concentration, pH, etc. of a surrounding medium in which the beads are suspended.

It may be possible to introduce physical characteristics into the cells during the incubation period by the use of a growth medium that contains a labeled, e.g. fluorescence or radio-labeled ingredient, and subsequently examining the beads for the label characteristic.

Methods of non-invasively examining the beads or their vicinity for differences in such characteristics are known and/or will be apparent to those skilled in the art. Generally methods of examination which are capable of automation are preferred to manual methods.

In the further step or steps of separation the beads may be separated manually, or more preferably automatically. Separation may follow an optional further step of incubation, e.g. to increase the amount of viable biomass.

In the further step of culturing and growing the viable cells, for example in a microtitre well, the beads may be incubated in an appropriate medium, as above, which may additionally include a solubilising agent for the polymer bead material, for example in the case of calcium alginate beads a calcium sequestrant such as a Cas-Amino Acid solution, tri-sodium citrate, or phosphate, among others. Solubilisation of the bead allows sufficient oxygen transfer to the biomass so that growth can continue within and ultimately beyond the bead. Conveniently each bead containing viable cells may be cultured individually for example in a microtitre well so that for example in the field of cell line development using mutagenesis, individual mutant cells may be cultured separately for subsequent screening for usefulness.

The method of the invention provides inter alia the advantage that by encapsulating the cells within the above-described beads they may be physically handled and separated by mechanical apparatus, so that the process can be automated for speed.

Accordingly, an apparatus for separating physically distinguishable particles is provided, comprising:

means for presenting the particles to a detection means which is adapted to non-invasively physically detect and distinguish individual particles into classes based upon physical characteristics of the particles or the adjacent vicinity of the particles;

particle directing means adapted to physically separate particles of one of said classes from those of another class, and;

control means adapted to control the particle directing means in response to the output of the said detection means.

Suitably in the apparatus the particles are transported and/or presented to the detection means in a flow of a fluid. Therefore suitably the apparatus also comprises a means for providing such a flow, for example a means for suspending the particles in a fluid and a means for causing this suspension to flow. Such a suspension provides a convenient handling vehicle for the particles, particularly the polymeric beads used in the above-described method of the invention.

As obtained from the above-described incubation process, such beads differ by being either empty of cells or contain only a non-viable cell or cells; or contain a multiplied growth of a viable cell or cells (but which may also contain one or more non-viable cells). Such beads may differ in their physical characteristics as described above.

The means for suspending the particles in a fluid may suitably comprise a suspension vessel to contain a suspension of the particles in a suspension fluid. If the particles are the above-describe ads, the fluid may suitably comprise water or the growth supporting medium. The suspension vessel may act as an incubation vessel, or the apparatus may comprise a separate suspension vessel into which the beads may be introduced following incubation. The fluid is preferably agitated to maintain the particles in suspension.

The detection means may comprise known detection instruments responsive to some suitable physical characteristic, such as those discussed above with reference to the beads, of the particles themselves or the adjacent suspension fluid.

Detection of particles and distinguishing of their class may be achieved by a single detection/distinguishing instrument which both detects them and distinguishes them, or by separate instruments to respectively detect and then separately distinguish the particles.

The detection means may be one which is inherently capable of distinguishing classes of particles, or alternatively may be capable of doing so after suitable control, e.g. calibration or programming, e.g. using a computer. Such a means may for example comprise a video camera monitoring the particles and cooperating with image processing equipment programmed to analyse the video image and distinguish between particles. Such calibration or programming may also be linked to the means for presenting the particles to the detection means, so that an optimum rate of flow and separation of the particles is achieved. This control may be individually set up for a particular purpose by operators of the apparatus within its operating parameters, for example to be sensitive to a desired level of growth of viable cells in the beads.

Optical detection means are suitable, which may comprise known optical instruments such as a light source with a photodetector mounted adjacent so as to detect the particles by transmissivity or reflectivity differences as the particles pass between the source and the detector, or into a position where light can be reflected from them at the detector, or a video microscope camera observing the particles as they enter its field of view, or other known type of optical detector which is capable of detecting the presence of a particle and distinguishing between classes of particles on the basis of their optical characteristics. A light source with a photodetector mounted opposite, sensitive to transmission changes as particles pass between is suitable. Such a light source may typically emit light in the visible region of the spectrum, and the detector may be sensitive to such radiation. Beads containing a biomass of multiplied viable cells are generally less optically transparent than beads which are empty of cells or contain non-viable cells.

When the particles are the above-described beads, two classes which may be distinguished by the detection means are: beads which are empty of cells or contain only non-viable cells; and beads which contain the biomass of viable multiplied cells. Two other classes which may be distinguished are beads which contain viable cells which differ in their degree of viability or their level of growth. Such classes may be distinguished on the basis of for example the absence, presence, amount or distribution of biomass within the bead.

In one embodiment the means for presenting the particles to a detection means may suitably comprise means for channeling suspension of the particles into one or more flow streams, in which streams the particles are individually serially disposed, the flow streams being directed into the vicinity of the detection means.

The means for channeling the suspension into a flow stream in which the particles are individually serially disposed may suitably comprise one or more flow tubes each with an open end submerged in the fluid and having a bore only slightly greater than the particle diameter, e.g. less than 2 particle diameters, suitably less than 1.5 particle diameters. The open end of the flow tube may remain in one position within the suspension vessel for example if the suspension or beads are agitated, or may alternatively be moveable within the suspension vessel. The suspension may be caused to flow into such flow tubes by known methods, for example the introduction of further fluid into the suspension vessel to displace the suspension into the flow tube, positive pressure applied to the suspension vessel, or negative (suction) pressure applied further along the apparatus. Displacement is preferred. It is desirable to ensure that the rate of flow of the suspension into the flow tube is substantially constant. It is desirable that the flow tube should be smoothly curved so that flow of particles is not impeded by sharp angles in the flow tube. In such a flow tube a serial flow of particles may be achieved at a known flow rate, and with a known average serial spacing of particles, which facilitates the operation of the detection means.

When the flow stream is within a flow tube as describe above, the detection means may be located within the flow tube or in or outside the tube walls. Alternatively the flow tube may direct the flow of suspension into a detection chamber, i.e a chamber containing the detection means. Conveniently if the detection means is/are optical detection means, or means which rely upon permeability to radiation, such means may be located outside the tube wall, adjacent to a region of tube wall which is transparent to the optical or other radiation, or in a detection chamber. If the detection means rely upon electrical characteristics, such means may comprise electrical probes mounted within the tube, or in the tube walls, or outside the tube walls, or in a detection chamber.

Having detected a particle in the flow tube and distinguished into which class the particle belongs, the output from the detection means, which will normally be an electronic signal, may be used to operate the particle directing means so as to physically separate the particles on the basis of selected class. Various particle directing means which can be used when the flow stream is within a flow tube will be apparent to those skilled in the art.

In a preferred particle-directing means, downstream of the detecting and distinguishing means the flow tube terminates at an open end, this open end being opposite a facing entrance opening in a particle catcher, so that a particle may travel from the open end of the flow tube into the entrance opening of the particle catcher across the gap between the open end into the entrance opening, the open end of the flow tube and/or the entrance opening being provided with flow control means to allow or prevent free passage of a particle from one to the other.

For example in one embodiment of flow control means the entrance opening of the particle catcher, and/or the open end of the flow tube may be moveable relative to each other in and out of a facing relationship so that particles may pass from the flow tube into the particle catcher when they are in the opposite facing relationship, but may not pass when they are out of the opposite facing relationship. Alternatively the open end of the flow tube and the entrance opening of the particle catcher may be in a fixed relationship relative to each other, and there may be a shutter or diverter moveable between them, such that the direct passage of a particle from the open end of the flow tube into the entrance opening of the particle catcher may be allowed or obstructed. Other forms of such flow control means will be apparent to those skilled in the art.

Suitably particles of interest, e.g. in the case of the above-mentioned beads those containing cells of interest, e.g. viable cells, are caused to pass in this manner into the particle catcher. This preferred form of particle directing means provides the advantage inter alia that the particles may be substantially separated from the accompanying fluid of the flow stream.

In a preferred form of the apparatus which includes the above-described flow tube and particle catcher, the open end of the flow tube and the entrance opening in the particle catcher are both within an area of positive atmospheric pressure, e.g. an increased air pressure in a manifold surround them, and the particle catcher communicates with an area of lower atmospheric pressure, for example an exit opening open to the ambient air. In this way the atmospheric pressure difference between the entrance opening of the catcher and its exit opening may assist in encouraging particles to enter the entrance opening, and in directing them towards the exit opening. The surrounding manifold may conveniently also serve to collect rejected particles.

A preferred form of such a particle catcher comprises a catcher which is moveable relative to a fixed flow tube, for example a flexible, swiveling, hinged or rotatable catcher in the form of a tube.

For example in an alternative construction the flow tube may be divided into a "Y" or otherwise forked tube arrangement with the flow of suspension along the stem towards the fork, with the detection means monitoring a part of this stem, and provided with diverter means to divert selected particles traveling along the stem toward the fork along selected limbs of the fork, one or more of the said limbs thereby comprising a particle catcher.

For example when a particle travels down the flow tube it may be diverted into one limb or another of the fork on the basis of class by a laterally applied fluidic pulse or gate mechanism to direct it along one or other of the limbs, and optionally propelled by the constant flow or addition of further fluid. For example in another method the flow of fluid may be diverted by a conventional type of two-way valve arrangement, closing off one line of flow whilst opening another to the fluid flow. For example in another method the flow of fluid may be diverted into different separate compartments of a moveable slide or rotatable wheel, from which compartments particles of interest may be removed, e.g. by being directed along an appropriate limb of the fork and collected.

The particle catcher preferably communicates with a particle director to direct caught particles to a collector. When the particle catcher is in the form of a tube as described above the particle director may conveniently comprise a downstream extension to the catcher tube along which particles may be directed by for example a positive atmospheric pressure difference along the extension, for example the positive air pressure applied to a manifold surrounding the open end of the flow tube and particle catcher, relative to an open end of the extension. It is desirable to avoid too great an air pressure difference between the manifold and the open end of the extension outside the apparatus which is at ambient air pressure, as the particles may then emerge with such force that they are damaged or are difficult to collect. Conveniently a region of the extension downstream of the open end of the particle catcher and upstream of the open end of the extension may be surrounded by a partial vacuum manifold so as to remove excess fluid from the particles and to reduce the effect of the air flow on the particle's movement, so as to decelerate the particles. The particles emerging from the open end of the extension may then be collected.

In each of the above-mentioned particle directing means, the mechanical operation of the particle directing means may be control-linked to the detection means so that the directing of the particle of interest occurs in response to detection and distinguishing of the class of the particle. Operation of the particle directing means suitably takes place after a time delay subsequent to detection calculated so that the particle has moved downstream into the vicinity of the particle directing means, for example based upon a known flow rate in the flow tube. Suitable mechanical means of moving the flow tube and/or particle catcher in and out of their opposite facing relationship, or operating the shutter or diverter, will be apparent to those skilled in the art, e.g. compressed air, an electromagnetic solenoid, or another form of mechanical linkage.

In a further embodiment the means for presenting the particles, e.g. the above-mentioned beads, to a detection means may suitably comprise one or more particle director probes in the form of particle gripping probes or suction probes. Suction probes may for example comprise tubular probes having one or more orifices therein of dimensions less than the diameter of the particles, each suction probe being capable of being positioned in the vicinity of the particles, and of having a sub-atmospheric pressure applied thereto such that the particles are sucked toward the orifice(s) of the suction probe and at least one particle is retained over each orifice in a substantially orifice-closing relationship, the retained particles then being presented to the detector.

Each suction probe may suitably comprise a tube of internal bore smaller than the diameter of the particles, an open end of the bore forming the orifice, the other end having a vacuum applied thereto.

Conveniently the probe itself may be moved into the vicinity of the particles, and a vacuum applied so as to suck particles onto the orifices, the resultant change in pressure indicating that orifices are closed by particles and being sensed by a control system.

The positioning of the suction probe(s) into the vicinity of the particles may be achieved in a number of ways. In one embodiment the probe(s) may simply be inserted into the suspension of particles in the suspension vessel. In another embodiment the suspension of particles may be channeled into one or more flow streams, similar to that described above, and the probe(s) may be inserted into the flow stream(s). Such flow stream(s) may be established by for example causing the suspension to flow along one or more channels, which may be open troughs, a table or flow tubes having access holes for the probe(s).

When particles have been retained on the probe the probe may be moved into the vicinity of the detection means so as to present each particle to a detection means. One or more detection means may be used, sequentially presented to each particle, or a sufficient number of detection means may be used to present each particle simultaneously to a detection means. Detection means as described above may be used.

Having detected a particle on an orifice, and distinguished into which class the particle belongs, the output from the detection means, which will normally be an electronic signal, may be used to operate the particle directing means so as to physically separate the particles on the basis of selected class.

Conveniently the particle directing means may comprise means to admit a fluid such as air, water or a reagent to the orifice so as to terminate the suction which retains the particle. The particle may then simply fall away from the orifice and be collected.

When the trough is in the form of a table, suitably the suspension may be caused to flow across the plate so that a 2-dimensional array of particles is formed. The detection means may suitably comprise a video camera and programmed image processing equipment, so that the video camera can distinguish between particles having a desired characteristic, e.g. beads containing the biomass of viable cells, and those which do not possess this characteristic, e.g. beads which either contain no cells or only non-viable cells. The image processing equipment may be linked to control equipment which controls a particle director probe, which may be directed to individual selected particles, and may then be used to remove particles from the array and direct them to collection. Such a probe may be a particle gripping or suction probe, similar to those described above, on which a particle may be picked from the array and retained by suction, then subsequently released by removal of the suction. Alternatively such a probe may be a blowing probe, which directs a jet or curtain of a fluid such as air at a particle and blows it away from the array to a place from where it may be collected.

Collected particles from the apparatus described above may be simply disposed of if they are not of any interest, for example beads containing no cells or beads containing non-viable cells, or if they are of interest they may be set aside for further examination, or subjected to appropriate further treatment. In the case of beads containing viable cells for example obtained following a mutagenic treatment, these will conventionally be subjected to further culturing and growth. In cell screening processes these heads may for example be cultured for utility screening by collecting them in wells in a microtitre plate. In the apparatus of this invention collection of the beads in a microtitre well may be achieved by directing a bead into a well from the apparatus, e.g. from the particle director or from a probe and then applying relative X-Y motion to the director, the probe and the plate so that the next bead falls into an adjacent well, and so on until a plate is filled, when it may be replaced by a fresh well and stacked and/or dosed with cell growth medium. This X-Y movement, replacement and stacking procedure may be achieved by conventional known automatic means, linked to the control means discussed above, e.g. by a computer.

Subsequently the growth of cells in the individual wells of the microtitre plate may be monitored by essentially conventional means such as a photometric assay of the quantity of biomass in each well. Thereafter the production of a useful product during cell growth may be assayed, again by essentially conventional means such as reaction of the product with an appropriate assay reagent.

It has surprisingly been found that the above-described apparatus enables a substantial increase in the rate of automated cell screening.

The invention consequently further provides a method for distinguishing between cells having different attributes, for example viable and non-viable cells, or cells having a different degree of viability or level of growth, which comprises;

encapsulating one or more cells from the culture within a polymeric bead;

incubating the cells within the bead in a growth-supporting medium for a time period sufficient for multiplication of viable cells within the bead;

then separating beads containing the biomass of multiplied viable cells having a selected attribute from beads which are empty or contain cells which do not have the selected attribute by using an apparatus as described above.

1. Encapsulation of Cells in Polymeric Beads

A known concentration of spores of *Penicillium chrysogenum* or *Streptomyces clavuligerus* are mutated for example by exposure to Far U.V. light, NTG, or to Gamma irradiation. A known volume of a known concentration of the mutated spore suspension is then added to a sterile solution of 2.5–3% sodium alginate. The combined solutions are gently mixed until the spores are evenly distributed throughout the sodium alginate. By knowing the concentration and viability of the mutated spore suspension it is possible to add sufficient spores to a particular volume of sodium alginate so that an optimal number of calcium alginate beads contain one viable spore.

Using a peristaltic pump, 1 liter of the sodium alginate/ spore suspension is pumped, via silicone tubing, through a needle assembly into 2.5 liters of a 0.1M sterile solution of calcium chloride contained in a fermenter vessel. As the sodium alginate/spore suspension is passed through the needle assembly droplets are formed which then harden, on contact with the calcium chloride, into calcium alginate beads. The calcium chloride solution is gently agitated by the use of a magnetic stirrer and follower. When all the beads have been formed they are left for a further hour to complete the hardening process after which time the calcium chloride solution is drained from the fermenter.

At this point the beads may be hardened further by the addition of 2.5 liters of 1.0M calcium chloride in which they are gently stirred for a further hour. The calcium chloride solution is once again drained from the fermenter. When the beads have been suitably hardened and the calcium chloride drained off they are washed. 2 liters of sterile de-ionised water are pumped into the fermentation vessel. The beads are stirred for 20 minutes and then the water is drained off. The washing procedure is repeated five times or until there is no measurable calcium in the water wash.

After the last water wash has been drained, 2.5 liters of sterile growth medium are pumped into the fermentation vessel. The beads are gently agitated, using a magnetic stirrer and follower, under positive air pressure provided by a sterile air supply flowing at 0.5 vessel volumes per minute. The beads are incubated at a suitable temperature, for example 26° C. until the spores have germinated and mycelial growth has visibly occurred within the bead. It is now possible to see that the beads in the fermenter contain either none, one, or more than one growth centre.

Examples of suitable growth media are Media 1 and 2 below:

| Medium 1. | |
|---|---|
| Dipotassium Hydrogen Phosphate | 0.07 g |
| Potassium Dihydrogen Phosphate | 0.13 g |
| Magnesium Sulphate (heptahydrate) | 0.20 g |
| Sodium Sulphate (decahydrate) | 0.20 g |
| Iron (II) Sulphate (heptahydrate) | 0.02 g |
| Manganese (II) Sulphate (tetrahydrate) | 0.01 g |
| Zinc Sulphate (heptahydrate) | 0.02 g |
| Copper (II) Sulphate (pentahydrate) | 0.02 g |
| L-Glutamic Acid Monosodium Salt | 0.55 g |
| Yeast Extract | 0.5 g |
| Lactose BP | 20.0 g |
| Calcium Chloride | 3.68 g |
| Water | to make up 1.0 L |

All of these ingredients are added with stirring to deionized distilled water. The pH should be 5.5. The mixture is made up to volume with deionized distilled water and if necessary made up into suitable aliquots. The medium should be sterilized by autoclaving for 15 minutes at 121° C.

| Medium 2. | |
|---|---|
| L.Asparaginase | 1.0 g |
| Dextrin | 5.0 g |
| Dipotassium Hydrogen Phosphate | 0.5 g |
| Magnesium Sulphate | 0.2 g |
| M5D Trace Elements | 1.0 ml |
| Water | to make up 1.0 L |

All of these ingredients are added with stirring to distilled deionized water, and stirring is maintained for 30–60 minutes. The pH should be 7.0. The mixture is then made up to volume with distilled deionized water. The medium should be sterilized by autoclaving for 15 minutes at 121° C.

2. Description of Apparatus

Figure 1:
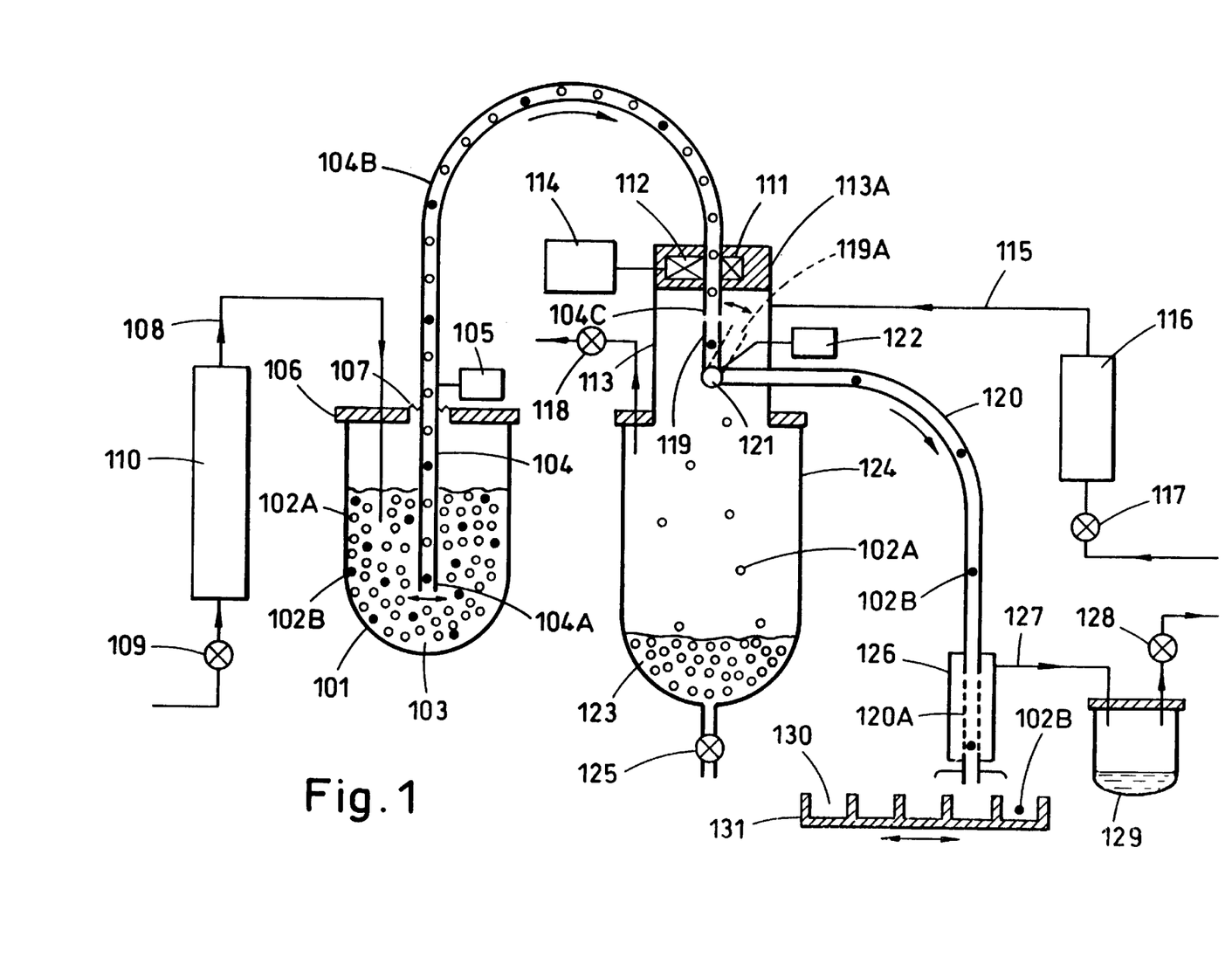
FIG. 1 which shows an apparatus of the invention in an overall schematic arrangement.

Referring to FIG. 1, an apparatus of this invention is shown overall but not to scale for clarity and to emphasise the principal features.

The apparatus comprises a suspension vessel (101) of ca. 5 liter volume into which has been introduced a suspension of polymeric beads (102) ca. 3 mm in diameter in suspension fluid (103) which may be water or growth medium. Beads (102) are either empty or contain non-viable cells (102A) or are beads containing the biomass of viable cells (102B), prepared in a growth medium as described in 1 above and which may have been subjected to an optional water washing step. A suspension concentration of around 50,000–80,000 beads $L^{-1}$ is typical.

The beads (102A, 102B) are kept in suspension by agitation of the suspension by movement of the open end (104A) of flow tube (104). Movement of the end (104A) of the flow tube (104) may be by means of a motor and mechanical link (105) acting on tube (104), which may for example pass through closure (106) of vessel (101) via a flexible bellows seal (107).

A stream of sterile water is introduced via feed (108), the flow of which is controlled by control (109). The water is sterile filtered by filter (110) before entering the vessel (101). The entry of water into vessel (101) causes a displacement of the suspension of beads (102A, 102B) into the flow tube (104), which is a tube of slightly greater internal diameter than the diameter of beads (102A, 102B) typically being 3.5–4.0 mm internal diameter. Within vessel (101) the tube (104) is made of stainless steel, and externally to vessel (101) is connected to a smoothly curving corresponding flow tube (104B) made of PVC which is transparent so as to assist observation of flow. An incoming flow rate in the range 100–750 ml/min. is typically used.

The flow tube (104B) passes between light source (111) and photodetector (112), mounted in the upper part (113A) of manifold (113). Between light source (111) and photodetector (112) the flow tube (104B) is optically transparent. When beads (102) flow between the light source (111) and detector (112) there is a change in the electronic output from detector (112), the change being different when the bead (102B) contains a high proportion of biomass resulting from viable cell growth, relative to when the bead (102A) contains non-viable cell(s) or no cells at all. The output of detector (112) is monitored by control (114). Typically a flow speed of around 17–130 cm/sec in the flow tube (104) is used. The serial separation of beads (102A, 102B) in flow tube (104) may typically be 0.5–4.0 cm. Flow tube (104A) terminates at an open end (104C) within manifold (113). Manifold (113) is maintained at a slight positive internal air pressure typically 1–2 psi via air inlet line (115) which admits sterile air filtered by filter (116) under the control of control (117). Excess air is bled off from manifold (113) via bleed valve (118).

Within manifold (113) is a particle catcher (119) in the form of a tube around 4.0 mm internal diameter. This is extended to form a director tube (120), the link between particle catcher (119) and direction tube (120) being rotatable at (121), so that particle catcher (119) can occupy two terminal positions (119) and (119A). In position (119) the open end of the particle catcher is opposite to the open end (104C) of the flow tube (104), in a facing relationship, whereas in position (119A) the open end of the particle catcher (119) is not in this relationship.

In operation therefore when a filled bead (102B) passes between light source (111) and detector (112) the monitored output is used to operate the control (122) of the particle catcher (119), mechanically linked to particle catcher (119) so as to move particle catcher (119) into terminal position (119) so that bead (102B) may fall into the open end of the particle catcher (119) as it falls from the open end (104C) of flow tube (104). This movement is performed at an electronically calculated time interval after the bead (102B) has passed between light source (111) and detector (112) so that the open end of particle catcher (119) is in position immediately before the bead (102B) reaches open end (104C) of the flow tube (104), and particle catcher (119) is held in position (119) for a time just long enough to receive bead (102B) before being returned to position (119A). The control (122) of director tube (119) may typically be an electronically activated solenoid (not shown) to control a pneumatic piston (not shown). The calculation of time period is based upon the velocity of the beads (102A), (102B) in flow tube (104) and the distance between detector (112) and open end (104C) of flow tube (104). The velocity of the beads (102A, 102B) in flow tube (104) may be calculated inter alia from the incoming flow through control (109) and the bore of tube (104).

When an empty bead or one containing non-viable cells (102A) passes between light source (111) and detector (112), particle catcher (119) is maintained in, or returned to, position (119A) so that such beads fall through manifold (113) to collect together with excess medium (123) in a collector (124) at the bottom of the manifold (113), from whence they can be disposed of through drain (125).

After beads (102B) have entered particle catcher (119) they are driven by the positive air pressure within manifold (113) into a flexible director tube (120). A lower part (120A) of director tube (120) is perforated and surrounded by a manifold (126) by which a partial vacuum typically 10 mbar is applied via vacuum line (127) controlled by control (128). This application of vacuum both decelerates beads (102B) and removes fluid, so drying the beads (102B). Excess fluid from the manifold is collected in vessel (129) from which it may be disposed of.

At the lower end (120A) of director tube (120) beads (102B) emerge and are arranged to fall into wells (130) of a microtitre plate (131) which can be automatically moved by control and drive means of generally known type (not shown), so that as each bad (102B) falls from lower end (120) there is an empty well (130) to receive it. By adjustment of the positive air pressure within manifold (113) and the vacuum applied to manifold (126) the velocity of the beads (102B) as they emerge at (120B) can be sufficiently low to avoid damage. It is important to balance the pressure applied by air line (115), the rate of bleed from bleed (118), the vacuum applied by line (127) and the inlet water flow along line (108) so that flow of beads in the indicated direction occurs, so that beads (102B) exit at 16B with a sufficiently low velocity to allow them to be collected in the wells (130). This can be easily achieved during setting up of the apparatus.

The automatic operation of plate (131) is linked inter alia to controls (114) and (122) so that when a filled bead (102B) is detected by detector (112) control (114) will only position particle catcher (119) when an empty well (130) is ready to receive bead (102B). Control (114) also directs the drive means (not shown) of plate (131) to move after a calculated time interval, based upon the known time for beads (102B) to travel from the vicinity of detector (112) to a receiving well (130), so that as soon as bead (102B) has come to rest in well (130) the well (130) containing it may be moved away from the open end (120B) of director tube (120) and a fresh empty well (130) is moved into place under open end (120A) ready to receive the next filled bead (102B). Drive means to apply the necessary X-Y motion to a plate (131) are known in the art. Conveniently X motion may be applied to open end (120B) and Y motion to plate (131).

Electronic control means such as that capable of calculating the time delay after the bead has passed detector (112) before operating control (122) and other control functions of the apparatus will be apparent to those skilled in the art, and may comprise a microprocessor (not shown). Such a control means may also operate controls (109), (117), (122) and (128) as well as the X-Y motion of microtitre plate (131).

3. Alternative Manifold Construction

Figure 2:
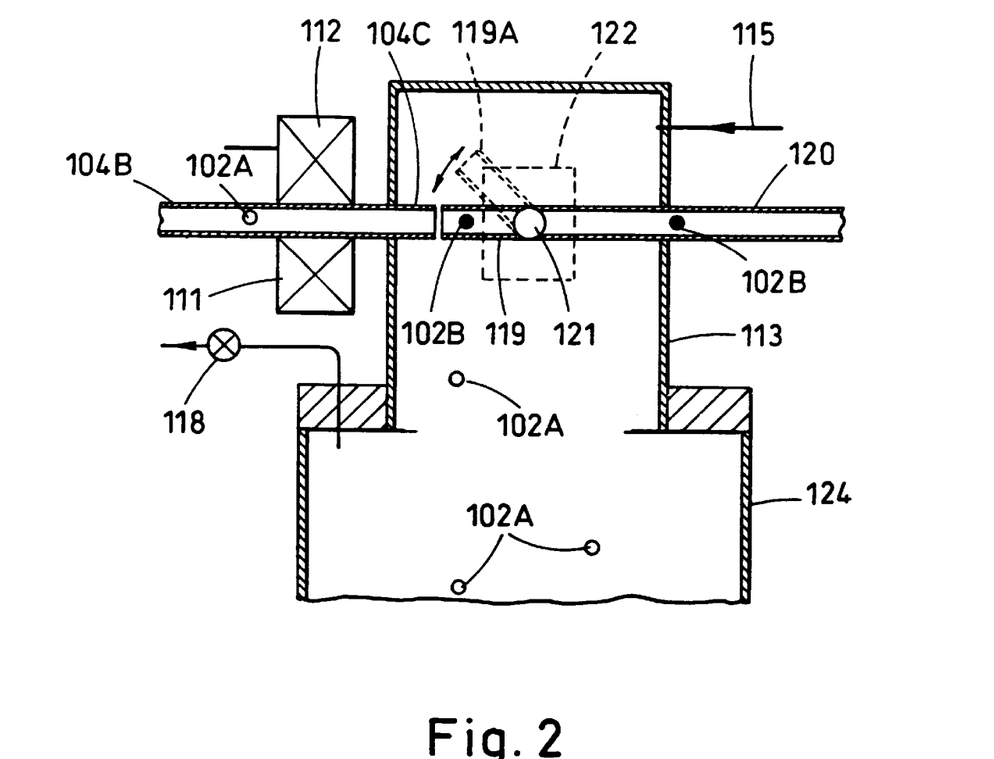
FIG. 2 which shows an alternative construction of the manifold of the apparatus of FIG. 1.

In FIG. 2 an alternative, preferred, construction of the manifold and associated parts of the apparatus of FIG. 1 is shown schematically. Parts in common with FIG. 1 are numbered in correspondence with FIG. 1. The manifold and parts shown in FIG. 2 operate generally analogously to the corresponding parts shown in FIG. 1.

Referring to FIG. 2, the flow tube (104B) passes between light source (111) and photodetector (112), as in FIG. 1, except that over this region flow tube (104) is horizontally arranged. The flow tube (104B) enters manifold (113) horizontally and terminates in an open end (104C).

Within manifold (113) is a particle catcher (119) in the form of a tube around 4.0 mm internal diameter. This is extended to form a director tube (120), the link between particle catcher (119) and direction tube (120) being rotatable at (121), so that particle catcher (119) can occupy two terminal positions (119) and (119A). In position (119) the open end of the particle catcher is opposite to the open end (104C) of the flow tube (104), in a facing relationship, whereas in position (119A) the open end of the particle catcher (119) is not in this relationship.

In operation therefore when a filled bead (102B) passes between light source (111) and detector (112) the monitored output is used to operate the control (122) of the particle catcher (119), via a mechanical link (not shown in FIG. 2) so as to move particle catcher (119) into terminal position (119) so that bead (102B) may pass into the open end of the particle catcher (119) across the narrow gap between the open end (104C) of flow tube (104) and the particle catcher (119). This movement is performed at an electronically calculated time interval after the bead (102B) has passed between light source (111) and detector (112) so that the open end of particle catcher (119) is in position immediately before the bead (102B) reaches open end (104C) of the flow tube (104), and particle catcher (119) is held in position (119) for a time just long enough to receive bead (102B) before being returned to position (119A). The control (122) of director tube (119) may typically be an electronically activated solenoid (not shown) to control a pneumatic piston (not shown). The calculation of time period is based upon the velocity of the beads (102A),(102B) in flow tube (104) and the distance between detector (111) and open end (104C) of flow tube (104). The velocity of the beads (102A, 102B) in flow tube (104) may be calculated inter alia from the incoming flow through control (109) and the bore of tube (104).

When an empty bead or one containing non-viable cells (102A) passes between light source (111) and detector (112), particle catcher (119) is maintained in, or returned to, position (119A) so that such beads fall through manifold (113) to collect together with excess medium (123) in a collector (124) at the bottom of the manifold (113), from whence they can be disposed of through drain (125).

4. Alternative Particle Directing Means

Figure 3A:
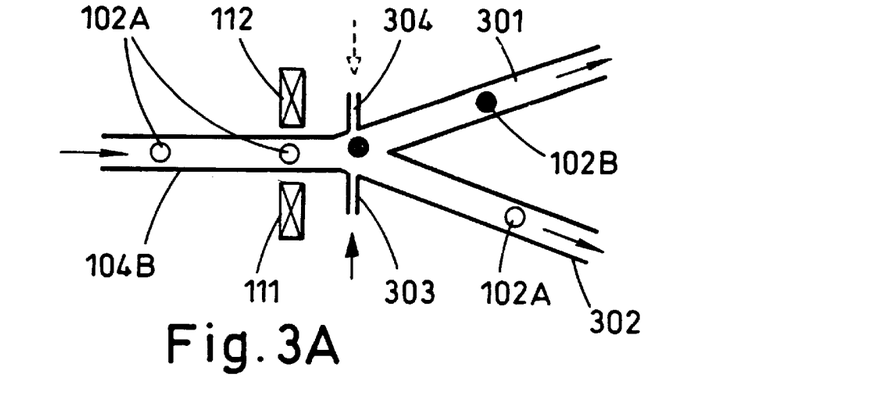
FIGS. 3A–C which show alternative forms of particle directing means for use in the apparatus of FIG. 1.
Figure 3B:
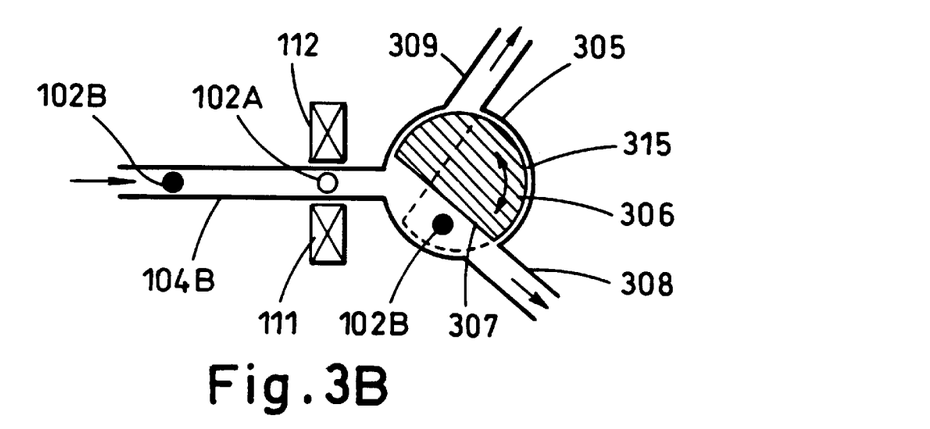
Figure 3C:
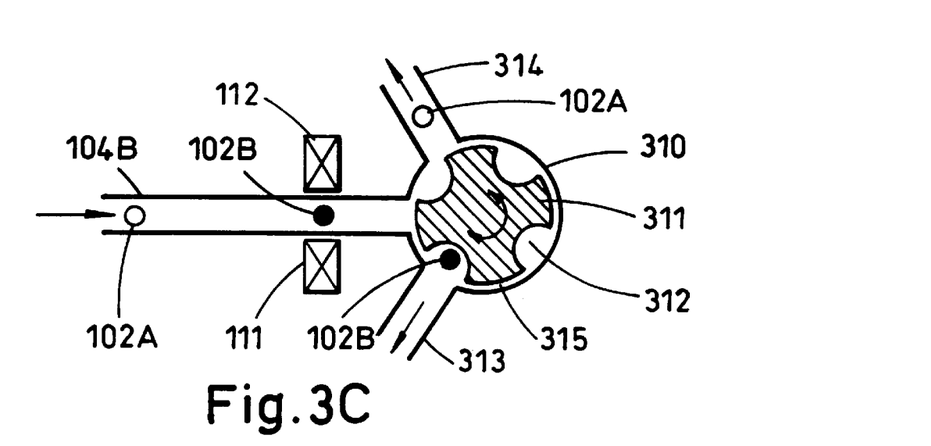

In FIG. 3, three alternative particle directing means comprising forked flow tubes are shown, which can be used to separate particles in the apparatus of the invention.

Referring to FIG. 3A, flow tube (104B) of the apparatus of FIG. 1 is divided to form a "Y" forked tube having limbs (301) and (302). The stem of the "Y" passes between light source (111) and detector (112). Immediately upstream of the division are located two fluidic injectors (303) and (304), opposite each other in the walls of flow tube (104), and in the plane of the "Y". When the detector (112) detects the presence of a bead (102B) containing the biomass of viable cells, after a time delay sufficient for bead (102B) to be slightly downstream of injector (303) a pulse of water is applied through the injector (303) to direct the bead (102B) into limb (301). Conversely by an analogous operation beads (102A) are directed by a pulse from injector (304) into limb (302). These pulses may be provided by a pump (not shown) operated by a control (not shown) analogous to control (122) of FIG. 1.

Limb (301) may be extended to form a director tube (not shown but analogous to (120) of FIG. 1) to lead beads (102B) towards a microtitre plate after excess fluid has been removed, for example by a surrounding vacuum manifold (not shown but in an arrangement similar to that (126) of FIG. 1), and air may be introduced with the beads (102A, 102B) to space them out along the "Y" tube. Limb (302) may be arranged to feed beads (102A) into a disposal system (not shown), analogous to drain (125) of FIG. 1.

Referring to FIG. 31B, flow tube (104B) of FIG. 1 feeds into a 2-way valve arrangement which comprises a cylindrical valve chamber (305) within which is a conforming valve plug (306) capable of rotating within chamber (305) and having a cut out channel (307) therein enabling the flow tube (104) to be brought into communication with either of two exit tubes (308) and (309) in a forked arrangement. Flow tube (104) passes between light source (111) and detector (112). In an operation analogous to that of the arrangement of FIG. 2A, when detector (112) detects a bead (102B) containing the biomass of viable cells, valve plug (306) is rotated so as to direct bead (102B) along exit tube (308). Conversely in an analogous operation empty beads (102A) may be directed along exit tube (309) by rotation of plug (306) into a position wherein the channel (307) is in the position shown by the hatched line of FIG. 31B. Exit tubes (308) and (309) may be extended into a director tube and for disposal of beads respectively in a manner analogous to FIG. 3A.

Referring to FIG. 3C, the arrangement and general operation is similar to that of FIG. 33, except that in place of the 2-way valve (305–309) arrangement there is a cylindrical chamber (310) within which there is a conforming cylindrical plug (311) having a number of indents (312) around its perimeter, which on rotation of plug (311) may be brought into communication with exit tubes (313), (314) in a forked arrangement. When detector (112) detects a bead (102B) containing the biomass of viable cells, plug (311) may be rotated after an appropriate time delay so as to capture the bead (102B), and then further rotated so as to introduce it into exit tube (313). Conversely beads containing non viable cells (102A) may be introduced into exit tube (314). Exit tubes (313) and (314) may be extended into a director tube and for disposal of beads respectively in a manner analogous to FIG. 3A.

The chambers (305), (310) suitably also include a peripheral gap (315) between the wall of the chamber (305), (310) and their respective plugs (306), (311) so that flow of fluid is not impeded.

4. Alternative Forms of Apparatus

Referring to FIG. 4, parts corresponding to FIG. 1 are numbered in correspondence. An apparatus of this invention is shown comprising a suspension vessel (401) containing a suspension (402) of polymeric beads ca. 3 mm in diameter which are either empty or contain non viable cells (102A), or are beads containing the biomass of multiplied viable cells (102B), prepared as described in 1 above.

Figure 4A:
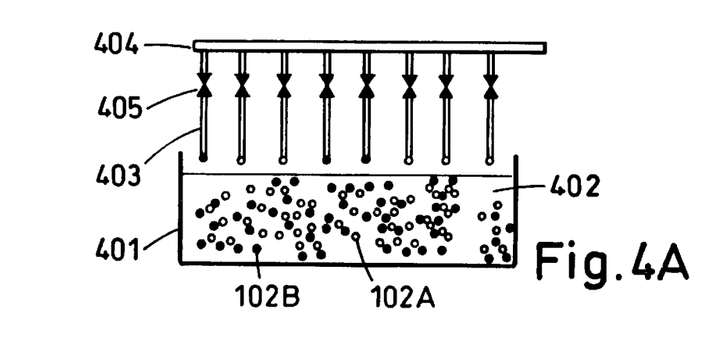
FIGS. 4A–F which show alternative forms of particle directing means.

The apparatus has a number of particle director probes which are suction probes (403) connected to a vacuum line (404), each probe (403) having a vacuum control valve (405). As shown in FIG. 4A, the probes (403) have been inserted into the suspension (402), and beads (102A) and (102B) have been sucked onto the open ends of probes (403), and are retained in place over the open ends of the probes (403) by suction, when the probe is removed from suspension (402).

Figure 4B:
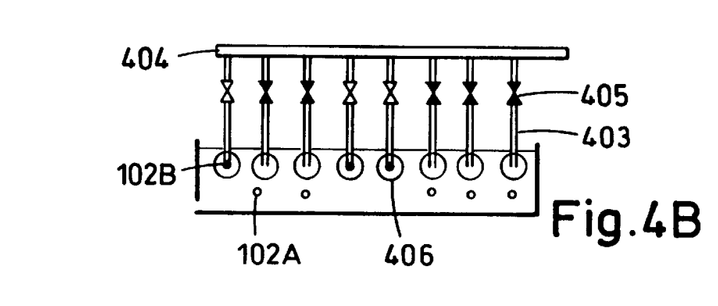

As shown in FIG. 4B, each probe (403) has been presented to a sensor (406), comprising a light source (not shown) and photo detector (not shown), between which the beads are positioned. Beads (102A) differ in their transmissivity to light from beads (102B), and this results in a differing electronic signal output from the detector (not shown). This differing signal is used to control the admission of air via valves (405) into the suction probes (403) on which are retained beads (102A), so that these beads fall from the probes (403), whilst a vacuum is maintained in the suction probes (403) on which are retained beads (102B), so as to retain them in place.

Figure 4C:
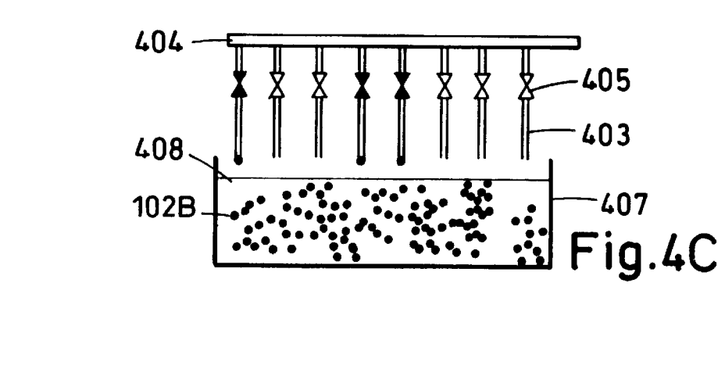

As shown in FIG. 4C, the suction probes (403), on which are retained only beads (102B), are moved into place over a collecting tank (407) (alternatively the tank may be moved while the probes remain stationary). Air is admitted via valves (405) into probes (403) on which are retained beads (102B), so as to cause beads (102B) to fall into the tank (407), which may contain a growth medium (408).

Alternatively a microtitre plate (not shown) may be used to collect the beads (102B). By positioning such a plate beneath the probes (403) and applying relative X-Y motion to the probes (403) and plate, and appropriately admitting air into probes (403) on which is retained a bead (102B), the beads (102B) may each be caused to fall individually into a well in the microtitre plate.

Figure 4D:
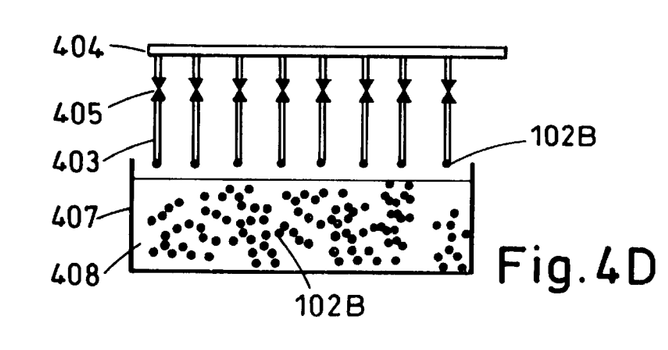
Figure 4E:
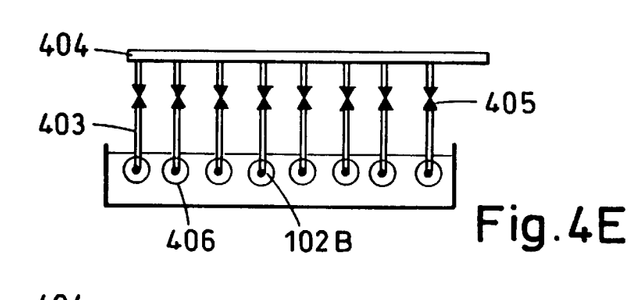

In an optional further step as shown in FIG. 4D, suction probes (403) may be reinserted into tank (407) and beads (102B) are sucked by the vacuum applied via manifold (404) onto the end of each of each probe (403). The presence of a bead on the end of each probe (403) may be checked by presentation to a sensor (406) as shown in FIG. 4E, similarly to the method described above with reference to FIG. 4B. Beads (102B) may then be caused to fail into wells in a microtitre plate (not shown) positioned beneath the open ends of the probes (403), by opening valves (405) and admitting air into the probes (403).

Figure 4F:
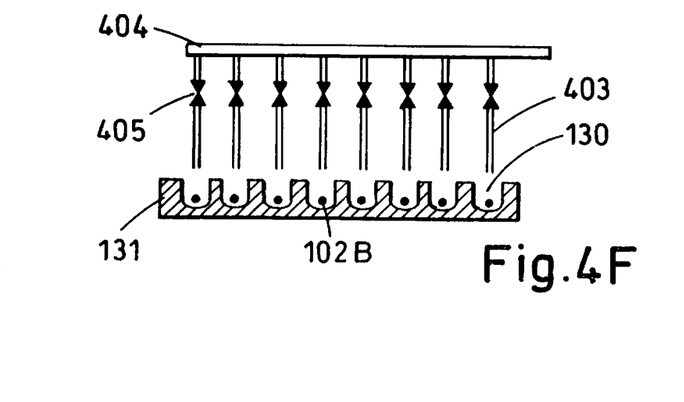

Referring to FIG. 4E, after a period of cell growth within the beads (102B) the probes (403) may be reinserted into the medium (408), and beads (102B) removed therefrom on the open ends of suction probes (403) in a manner analogous to that described above. The beads (102B) may then be presented to sensors (406) which detect the presence of an increased amount of biomass within beads (102B). The probes (403) plus beads (102B) may then be moved into position over wells (130) in a microtitre plate (131) and the beads (102) allowed to drop into the wells (130), as shown in FIG. 4F.

Figure 5:
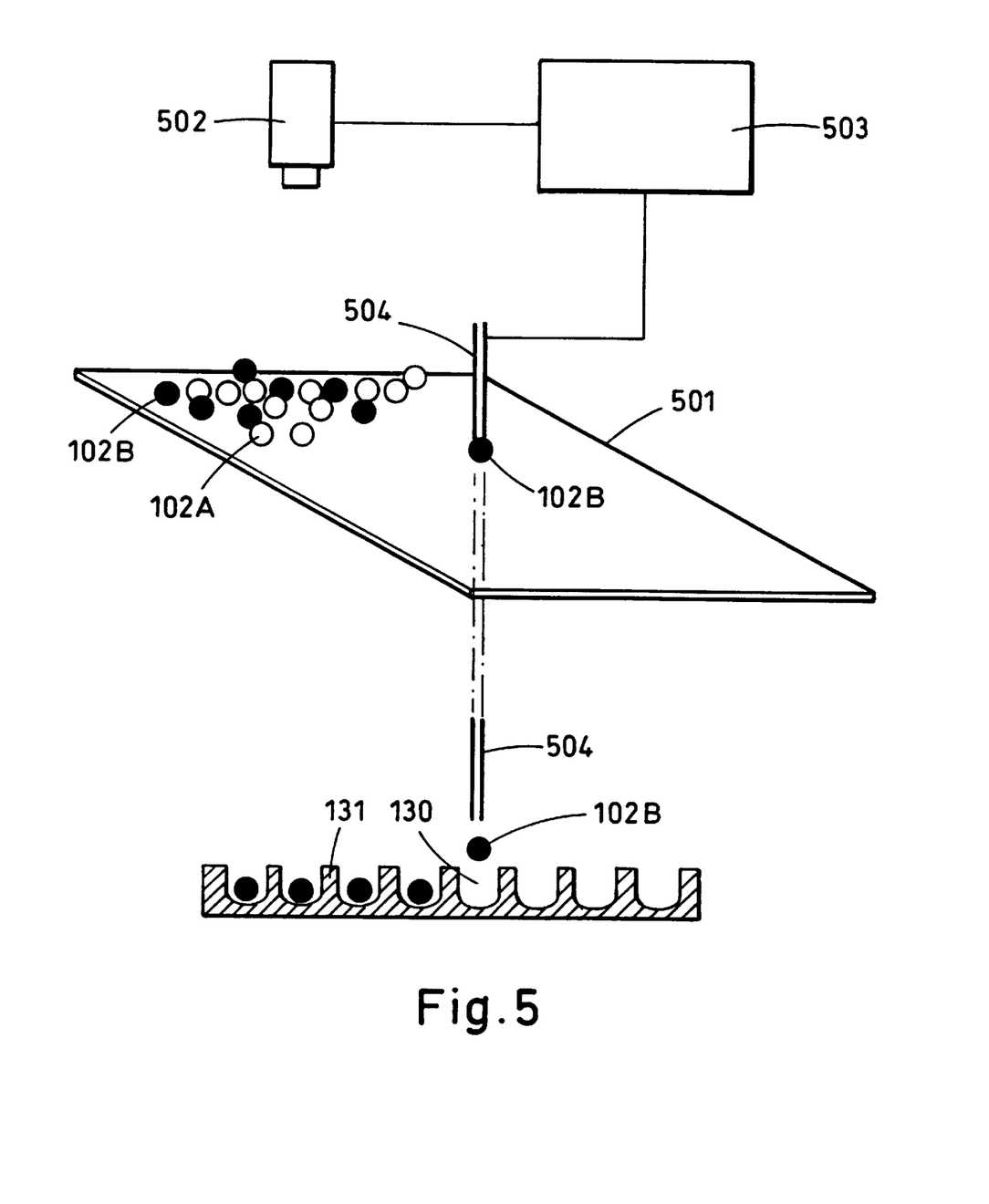
FIG. 5 which shows a further alternative form of particle directing means.

Referring to FIG. 5, parts corresponding to FIG. 1 are numbered in correspondence. An apparatus of this invention comprises a table (501) on which is a 2-dimensional array of beads prepared as described in 1 above, which either contain no cells or contain non viable cells (102A), or contain the biomass of viable cells (102B).

A video camera (502) is positioned above the table (501) and monitors the array of beads (102A, 102B). The camera (502) is connected to image processing and control equipment (503), and to a particle director probe (504) which is a tube connected to a vacuum manifold (not shown). The video camera (502) and image processing equipment (503) detect the differing visual appearance of beads (102A) and (102B) and the control equipment (503) directs the probe (504) to beads (102B) containing the biomass of multiplied cells. The vacuum within probe (504) draws the bead (102B) to the open end of the probe (504) and retains it there by suction. The control equipment (503) then directs the probe (504) plus bead (102B) into a position above a vacant well (130) of a microtitre plate (131) as shown in FIG. 4B. The admission of air into probe (504) causes the bead (102B) to fall into the well (130). By the application of relative X-Y motion to the probe (504) and the microtitre plate (131) the plate (131) may be moved so that as the above-described process is repeated a fresh vacant well (130) is in position beneath the probe (504) to receive a fresh bead (102B).

Figure 6:
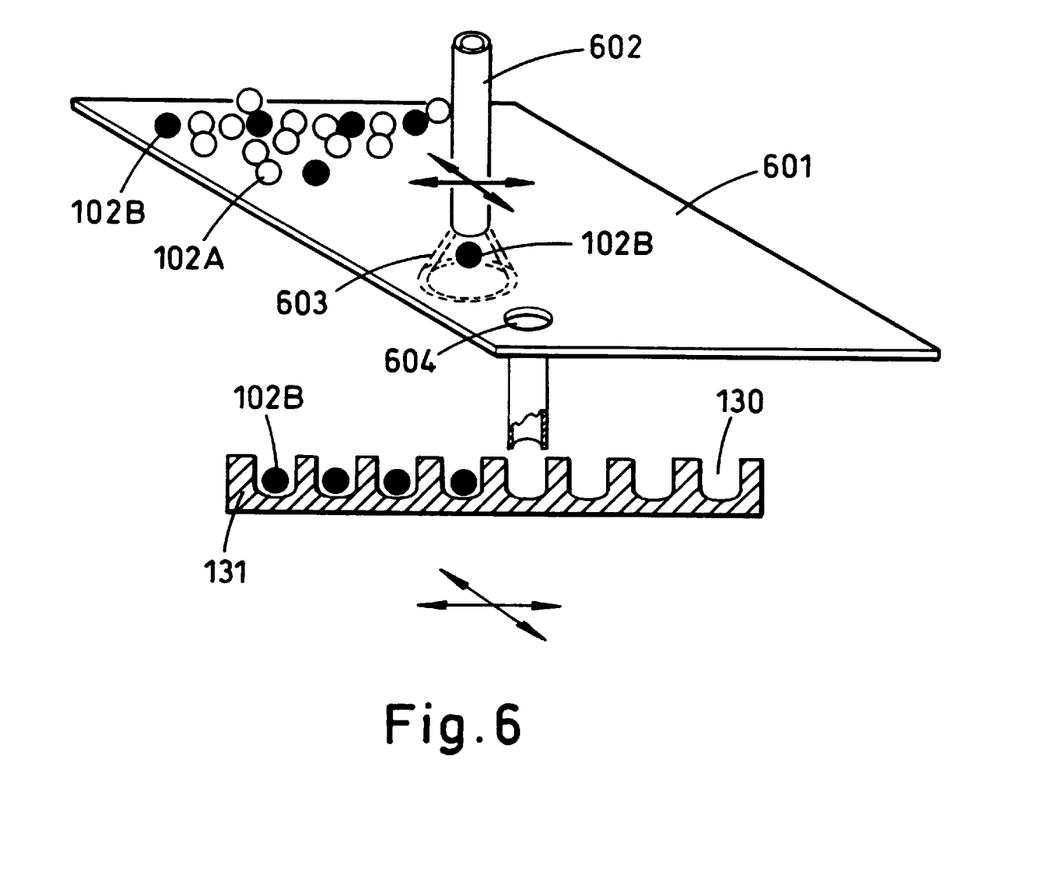
FIG. 6 which shows a further alternative form of particle directing means.

Referring to FIG. 6, parts corresponding to FIG. 1 are numbered in correspondence. An apparatus of this invention comprises a table (601) on which is a 2-dimensional array of beads (102A) and (102B) prepared as described in 1 above, being either empty (102A) or containing the biomass of viable cells (102B).

Using an arrangement of a video camera, image processing and control equipment (not shown) similar to that shown in FIG. 5, a particle director probe (602) is directed to beads of interest (102B). Probe (602) directs a cylindrical curtain of blown air (603) around a bead (102B), and this curtain (603) retains bead (102B) in the vicinity of probe (602). Probe (602) is then moved by the control means (not shown) to a position above hole (604) in table (601) bringing bead (102B) with it, upon which bead (102B) falls through the hole (604) into a well (130) in microtitre plate (131). By the application of relative X-Y motion to table and plate (131) the plate (131) may be moved so that as the above described process is repeated a fresh vacant well (130) is in position beneath hole (604) to receive a fresh bead (102B).

5. Culturing and Growing Viable Cells on a Larger Scale

Within the wells (130) in microtitre plates (131) beads (102B) which contain the biomass of multiplied viable cells may be grown on a larger scale so as to obtain more of the grown cells for examination. This is achieved by introducing into well (130) an appropriate medium, such as in 1 above, which includes a solubilizing agent for the polymer bead material, for example in the case of calcium alginate beads a calcium sequestrant such as a Cas-Amino Acid solution, tri-sodium citrate, or phosphate. Sufficient medium is introduced initially such that the bead (102B) is only partly submerged, so that oxygen transfer can occur. When sufficient growth of the cells within the bead (102B) has occurred such that the cell growth erupts out of the part of the bead (102B) which is above the surface of the medium, further medium is introduced to cover the bead (102B) and the cell growth. As further growth occurs it then takes place within or at the surface of the medium, beyond the confines of the bead. The time taken for this to occur will vary from cell strain to cell strain and can be determined experimentally by those skilled in the art.

We claim:

1. An apparatus for separating physically distinguishable polymeric beads at least some of which contain encapsulated cells possessing a selected attribute, comprising:

a vessel containing a suspension of the polymeric beads, at least some of which contain encapsulated cells possessing a selected attribute, in a suspension fluid;

means for presenting the beads to a detection means which is adapted to non-invasively physically detect and distinguish individual beads into classes based upon physical characteristics of the beads or the suspension fluid in the adjacent vicinity of the beads;

particle directing means adapted to physically separate beads of one of said classes from those of another class, and;

control means adapted to control the bead directing means in response to the output of the said detection means so as to direct each bead to a defined destination.

2. An apparatus according to claim 1 wherein the beads are transported and/or presented to the detection means in a flow of the suspension fluid.

3. An apparatus according to claim 2 wherein the means for presenting the beads to a detection means comprises means for channeling the suspension into one or more flow streams, in which streams the beads are individually serially disposed, the flow streams being directed into the vicinity of the detection means.

4. An apparatus according to claim 3 wherein the means for channeling the suspension into a flow stream in which the beads are individually serially disposed and comprise one or more flow tubes having a bore less than 2 bead diameters.

5. An apparatus according to claim 4 wherein downstream of the detecting and distinguishing means the flow tube terminates at an open end, this open end being opposite a facing entrance opening in a bead catcher, so that a bead may travel from the open end of the flow tube into the entrance opening of the bead catcher across the gap between the open end into the entrance opening, the open end of the flow tube and/or the entrance opening being provided with flow control means to allow or prevent passage of a bead from the open end of the flow tube to the said entrance opening.

6. An apparatus according to claim 5 wherein the entrance opening of the bead catcher, and/or the open end of the flow tube are moveable relative to each other in and out of a facing relationship so that beads may pass from the flow tube into the bead catcher when they are in the opposite facing relationship, but may not when they are out of the opposite facing relationship.

7. An apparatus according to claim 6 wherein the open end of the flow tube and the entrance opening in the bead catcher are both within an area of positive atmospheric pressure, and the bead catcher communicates with an area of lower atmospheric pressure.

8. An apparatus according to claim 4 wherein the flow tube is divided into a "Y" or otherwise forked tube arrangement with the flow of suspension along the stem towards the fork, with the detection means, monitoring a part of this stem, and provided with diverter means to divert selected beads traveling along the stem toward the fork along selected limbs of the fork one or more of the said limbs thereby comprising a bead catcher.

9. An apparatus according to claim 5 wherein the bead catcher communicates with a bead director to direct caught beads to a collector.

10. An apparatus according to claim 9 wherein the bead director comprises a downstream extension to the bead catcher along which particles may be directed by a positive atmospheric pressure difference along the extension.

11. An apparatus according to claim 10 wherein a region of the extension downstream of the open end of the bead catcher and upstream of the end of the extension is surrounded by a partial vacuum manifold.

12. An apparatus according to claim 1 wherein the detection means is an optical detection means.

13. A method for distinguishing between cells having different attributes, comprising;

encapsulating one or more cells from the culture within a polymeric bead;

incubating the cells within the bead in a growth-supporting medium for a time period sufficient for multiplication of viable cells within the bead;

then separating beads containing the biomass of multiplied viable cells having a selected attribute from beads which are empty or contain cells which do not have the selected attribute, by using the apparatus of claim 1.

14. An apparatus for separating physically distinguishable polymeric beads, comprising:

means for suspending the polymeric beads in a suspension liquid and to form a suspension of the beads in the suspension fluid, means for channeling the suspension of beads into one or more flow tubes each having a bore less than two bead diameters and in which streams the beads are individually serially disposed, the flow streams being directed into the vicinity of the detection means, means for presenting the beads to a detection means which is adapted to non-invasively physically detect and distinguish individual beads into classes based upon physical characteristics of the beads or the adjacent vicinity of the beads;

bead directing means adapted to physically separate beads of one of said classes from those of another class, and;

control means adapted to control the bead directing means in response to the output of the said detection means so as to direct each bead to a defined destination.

15. An apparatus for separating physically distinguishable polymeric beads, comprising:

means for suspending the polymeric beads in a suspension liquid and to form a suspension of the beads in the suspension fluid, a detection means which is adapted to non-invasively physically detect and distinguish individual beads into classes based upon physical characteristics of the beads or the suspension fluid in the adjacent vicinity of the beads, means for channeling the suspension of beads into one or more flow tubes in which streams the beads are individually serially disposed, the streams being directed to the detection means, means for presenting the beads to the detection means;

downstream of the detecting and distinguishing means the flow tube terminating at an open end;

a bead catcher having an entrance opening in a facing relationship to said open end, so that a bead may travel from the open end of the flow tube into the entrance opening of the bead catcher, flow control means provided at the open end of the flow tube and/or the entrance opening of the bead catcher to allow or prevent passage of a bead from the open end of the flow tube to the said entrance opening, a bead director tube in communication with the entrance opening of the particle catcher, the entrance opening of the bead catcher being at a higher atmospheric pressure relative to the bead director tube such that beads entering the entrance opening of the bead catcher are directed by the difference in relative air pressure along the bead director tube.

* * * * *